United States Patent [19]

Ohmura et al.

[11] Patent Number: 5,294,699
[45] Date of Patent: Mar. 15, 1994

[54] INHIBITION OF COLORATION OF HUMAN SERUM ALBUMIN

[75] Inventors: Takao Ohmura; Akinori Sumi; Wataru Ohtani; Naoto Fuluhata; Kaoru Kobayashi; Shinobu Kuwae; Hirotoshi Fukutsuka; Tomoshi Ohya; Hiroshi Morise, all of Osaka, Japan

[73] Assignee: The Green Cross Corporation, Osaka, Japan

[21] Appl. No.: 719,443

[22] Filed: Jun. 24, 1991

[30] Foreign Application Priority Data

Jun. 25, 1990 [JP] Japan .................. 2-166091

[51] Int. Cl.$^5$ .................. C07K 3/28; C12N 15/14; A61K 45/02
[52] U.S. Cl. .................. 530/364; 435/69.6; 435/70.1
[58] Field of Search .................. 435/69.6, 70.1; 530/364

[56] References Cited

U.S. PATENT DOCUMENTS 4,289,690 9/1981 Pestka et al. .................. 530/351
4,990,447 2/1991 König .................. 435/71.1

FOREIGN PATENT DOCUMENTS 0319067 of 0000 European Pat. Off. .
0319641 6/1989 European Pat. Off. .
0399455 11/1990 European Pat. Off. .

OTHER PUBLICATIONS

Chemical Abstracts, vol. 95, No. 15, Oct. 12, 1981, Columbus, Ohio; Abstract No. 127700V, U. Kragh–Hansen, "Effects of Aliphatic Fatty Acids . . . Albumin", p. 205.

Chemical Abstracts, vol. 104, No. 7, Feb. 17, 1986, Columbus, Ohio, Abstract No. 49748E, H. Gao et al., "Decolorization with Activated Carbon", p. 422.

Primary Examiner—Howard E. Schain
Assistant Examiner—P. Lynn Touzeau
Attorney, Agent, or Firm—Sughrue, Mion, Zinn, Macpeak & Seas

[57] ABSTRACT

A method of inhibiting the coloration of human serum albumin expressed by using the gene manipulation technology which method comprises separating coloring contaminants from said human serum albumin before said coloring contaminants bind to the human serum albumin.

10 Claims, 1 Drawing Sheet

INHIBITION OF COLORATION OF HUMAN SERUM ALBUMIN

FIELD OF THE INVENTION

This invention relates to a method of inhibiting coloration of genetically engineered human serum albumin.

BACKGROUND OF THE INVENTION

Albumin, in particular human serum albumin (hereinafter denoted as "HSA"), is a principal protein of blood plasma. The protein is produced in the liver and has a crucial role in maintaining normal osmotic pressure in the circulatory system. HSA also functions as a carrier for various serum molecules.

HSA is administered to patients in various clinical situations. For example, patients with shock or burn generally require repeated administration of HSA for restoring normal blood volume and thereby alleviating certain trauma-associated symptoms. Patients with hypoproteinemia or fetal erythroblastosis may require treatment with HSA. Therefore the basic therapeutic significance of HSA administration lies in treatment of fluid loss, for example in surgical operation, shock, burn or edema-inducing hypoproteinemia.

At present, HSA is produced primarily by fractionation of collected blood. The production method is disadvantageous because it is uneconomical and blood increasingly is difficult to procure. Furthermore, blood may contain unwelcome substances, for example hepatitis viruses. Accordingly, it will be helpful to develop an alternative source of HSA.

Meanwhile, the advent of recombinant DNA technology has made it possible to produce a variety of useful polypeptides in microorganisms. A number of mammalian polypeptides, for example human growth hormone and interferons have been produced in various microorganisms. The recombinant proteins have a variety of uses, such as vaccines, hormones, enzymes and antibodies.

To overcome some of the above-mentioned difficulties in the production of HSA, methods of producing HSA in large quantities using genetic engineering techniques and highly purifying the recombinant HSA have been attempted.

However, while serum-derived HSA originally has a yellow or yellowish brown color, genetically engineered HSA has a dark yellow or dark yellowish brown color. Raw materials contain certain coloring contaminants that bind to the HSA causing coloration of HSA during the production and purification thereof. The contaminants cannot be removed to a satisfactory extent by known methods of purifying serum-derived HSA.

SUMMARY OF THE INVENTION

It was found that coloration of human serum albumin can be prevented when coloring contaminants are removed before intracellular or extracellular genetically engineered HSA binds to the coloring contaminants.

An object of the present invention is to provide a method of preventing coloration of human serum albumin which comprises separating coloring contaminants from genetically engineered human serum albumin before said coloring contaminants bind to the human serum albumin and further provides a method of preventing coloration of human serum albumin which comprises employing, as a means for separating coloring contaminants from human serum albumin, at least one member of the group consisting of anion exchangers, hydrophobic carriers and activated charcoal.

DETAILED DESCRIPTION OF THE INVENTION

Figure 1B:
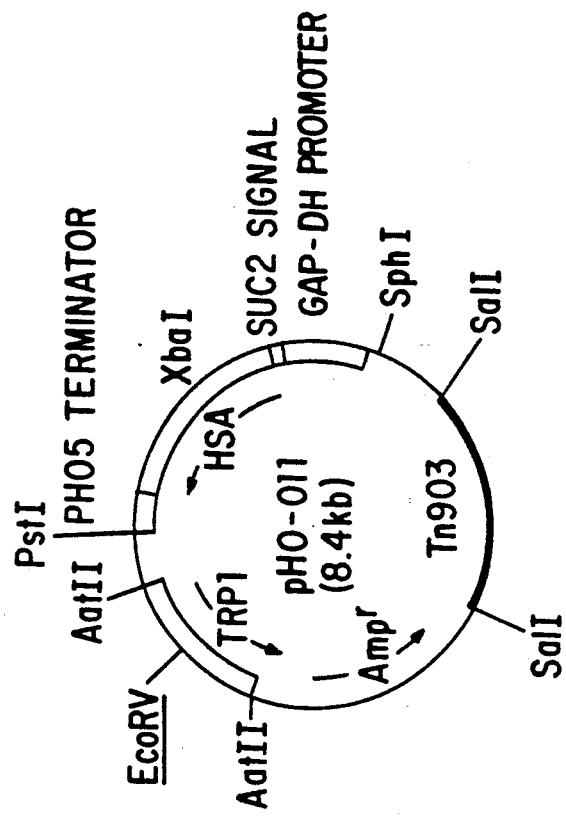
FIG. 1(a) and FIG. 1(b) depict maps of plasmids pMM-006 and pHO-011, respectively.

Any genetically engineered HSA species can be used without any particular limitation in the practice of the invention. Thus, HSA is produced in the manner of intracellular or extracellular expression (secretory expression) by cultivating cells genetically engineered and capable of expressing HSA. Such cells include *Escherichia coli*, yeasts, *Bacillus subtilis* and animal cells.

In the case of intracellular expression, the step of separating coloring contaminants from human serum albumin desirably should be carried out on the occasion of and/or immediately after obtaining said human serum albumin from cells and, in the case of extracellular expression, said step desirably should be conducted during the cultivation step.

The term "coloring contaminants" as used herein includes, within the meaning thereof, not only culture medium-derived coloring contaminants but also any and all substances capable of coloring HSA.

(i) Preparation of Cells for HSA Expression by Gene Manipulation

A method of preparing an HSA-producing yeast strain, which is taken as an example of the cell strain for HSA expression, is described as follows.

In the practice of the invention, the HSA-producing yeast strain is a yeast strain transformed with a plasmid carrying the HSA gene. The plasmid carrying the HSA gene can be prepared by appropriate techniques known in the art. Specifically, the plasmid contains an HSA gene, a promoter, a signal sequence, a terminator and so forth.

The albumin-encoding region contained in the plasmid is particularly a DNA sequence identical or substantially homologous to the HSA gene sequence, which can be obtained, for example from an optionally selected human cell line capable of producing HSA. Said DNA is a chromosomal DNA or a cDNA (complementary DNA). The chromosomal DNA can be separated from an HSA gene-containing genomic library and the HSA cDNA can be prepared in a conventional manner using mRNA.

The promoter is derived from the genomic DNA of yeast, preferably *Saccharomyces cerevisiae*. The use of a high expression yeast promoter is preferred. Suitable promoter sequences include those that regulate the TRPI gene, ADHI or ADHII gene, acid phosphatase (PHO3 or PHO5) gene, isocytochrome C gene, a gene of the galactose metabolizing system (GAL1, GAL10 or GAL7), the invertase gene (SUC2), a gene coding for a glycolytic system enzyme, such as enolase, glyceraldehyde-3-phosphate dehydrogenase (GAPDH), 3-phosphoglycerate kinase (PGK), hexokinase, pyruvate decarboxylase, phosphofructokinase, glucose-6-phosphate isomerase, 3-phosphoglycerate mutase, pyruvate kinase, triphosphate isomerase, phosphoglucose isomerase or glucokinase, or the yeast conjugation pheromone gene coding the a-factor or α-factor.

In a further preferred mode of gene manipulation, a signal sequence is incorporated into the construct plasmid. Usable as the signal sequence are yeast-derived signal sequences such as those associated with the invertase and α-factor genes. The signal sequence for HSA is preferable. A synthesized yeast signal sequence for secretory expression (EP-A-319641 and JP-A-1-240191 (the term "JP-A" herein used means a unexamined published Japanese Patent Application)9 corresponding to EP-A-329127) can be used.

As a result of introduction of this signal sequence, the HSA gene expression product enters the secretory pathway and is transported to the periplasmic space. Ultimately, secretion through the cell membrane into the culture medium occurs and a considerable increase in yield can be obtained. Further, because cells need not be disrupted, the recovery step can be simplified.

The plasmid further contains an appropriate sequence for the termination of transcription, for example the PHO5 or GAP-DH terminator.

In the practice of the invention, yeasts, in particular strains of the genus Saccharomyces or Pichia, are preferable as the host. Among them, auxotrophic strains and antibiotic-sensitive strains are preferred. The leucine-requiring, histidine-requiring and G418-sensitive strain Saccharomyces cerevisiae AH22 (a, his4, leu2, can1) and the like are preferred.

The method of transformation includes, among others, direct introduction of the plasmid into host cells and integration of the plasmid into a yeast genome.

The former method is carried out by known methods such as calcium phosphate microcoprecipitation, polyethylene glycol treatment of protoplasts or electroporation (EP-A-399455).

An HSA-producing yeast strain with the plasmid integrated in the yeast genome is used preferably in the practice of the invention. The plasmid contains a DNA sequence of part of a gene occurring naturally in the host yeast genome (for example, LEU2, HIS4, TRP1, URA3, ribosome DNA gene etc.). The homologous sequence enhances the likelihood of the whole plasmid or a linear fragment thereof integrating stably into the host genome. The modification enables the culture of descendant cells stably retaining the introduced genetic material during proliferation in the absence of a selective pressure. Thus, a plasmid containing a sequence naturally occurring in a yeast chromosomal gene together with the HSA gene can be integrated into the locus of said chromosomal gene and retained stably.

More specifically, it is desirable that the plasmid be cleaved at a site in the sequence that is homologous to the host yeast cell genome by restriction enzyme treatment and the linearized plasmid be introduced into the host. The linearized plasmid is integrated into the region on the host yeast cell chromosome that is homologous to the region inserted into the plasmid. The linearized plasmid is integrated into the host chromosome with increased frequency as compared with a circular plasmid.

Usable as the sequence homologous to a host yeast chromosomal sequence are, in particular, amino acid-synthesizing or nucleic acid-synthesizing genes, ribosomal DNAs, the Ty factor (transposon element of yeast) and the like. In a preferred embodiment, the host yeast is an amino acid-requiring or nucleic acid-requiring strain, namely a strain deficient in an amino acid-synthesizing system gene or nucleic acid-synthesizing system gene. In that case, the cloned transfected amino acid-synthesizing system gene or nucleic acid-synthesizing system gene serves to cure the mutation in the host and therefore can be used as a marker for transformant selection. As amino acid-synthesizing system or nucleic acid-synthesizing system genes rendering an auxotrophic host yeast prototrophic, the artisan may consider, for instance, LEU2, HIS4, TRP1 and URA3.

In addition to such amino acid- or nucleic acid-synthesizing system genes suited for use in cases where the host yeast is an auxotorophic strain, antibiotic resistance genes such as those providing resistance to cycloheximide, G418, chloramphenicol, bleomycin, hygromycin and other antibiotics, can be used as a selective marker in cases where the host is an antibiotic-sensitive strain.

The plasmid is incapable of autonomous replication in host yeasts. It is substantially free of a region for autonomous replication initiation in host yeasts, for example the origin of replication of 2 μm DNA or an autonomously replicating sequence (ARS).

The plasmid may contain an origin of replication and one or more selective markers, each capable of functioning in bacterial hosts, in particular Escherichia coli, in addition to the above-mentioned promoter, HSA-encoding region and region homologous to a yeast genomic sequence. Useful features lie in the use of such origin of replication to function in Escherichia coli and one or more selective markers for Escherichia coli in the yeast hybrid vector. Thus, hybrid vector DNA can be obtained in large amounts by multiplication of and replication in Escherichia coli. Secondly, hybrid vector construction can be made with ease by using established cloning techniques in Escherichia coli. Escherichia coli plasmids, for example pBR322, contain an origin of replication that is functional in Escherichia coli and one or more selective markers for Escherichia coli which provide resistance to antibiotics, such as tetracycline and ampicillin, can be used advantageously as a part of a yeast hybrid vector.

The plasmid thus contains a promoter, an HSA-encoding region regulated by said promoter, a sequence following the coding region for terminating transcription and a sequence homologous to a host yeast genomic sequence. As desired, the plasmid may further contain a signal sequence for secretory production, one or more selective markers for yeasts, an origin of replication to serve in Escherichia coli. and one or more selective markers for Escherichia coli. The plasmid is substantially free of an origin of replication to serve in yeasts.

Whether the plasmid has been integrated into the genome and whether the gene introduced is stable are then determined. Specifically, integration at the expected locus can be confirmed by Southern blotting using as a probe the host yeast cell chromosomal sequence used for transformation. The stability of the albumin-encoding gene can be confirmed by establishing that albumin production and maintenance of prototrophism are maintained after subculturing of the transformant over several generations in non-selective medium.

The transformant can be used again as the host for transformation with a second plasmid containing a HSA-encoding region. In this case, the region of the plasmid carrying yeast genomic sequences is homologous to a gene other than used in the first transformation.

Other host yeast cell genomic sequence that are suitable include ribosomal DNA and Ty factor which are present in multiple copies in each genome. Therefore, it would be possible to integrate the desired gene at a plurality of loci in the host genome by one transformation procedure. Alternatively, if a mutant requiring a number of nutrients and showing resistance to a number of antibiotics can be obtained, it will be possible to introduce a useful gene at a plurality of regions in the host genome.

Thus, the desired gene can be inserted into a plurality of regions on the host chromosome. The genes integrated in the chromosome are not lost but are retained stably. Integration of a plurality of genes makes it possible to produce the desired product in large amounts.

Alternately, an HSA-producing yeast can be prepared using heterokaryons obtained by cell fusion of a plurality of the above-described transformants (EP-A-409156).

The transformant is cultivated in a known medium, for example YPD liquid medium [1% yeast extract (Difco), 2% Bactopolypeptone (Difco), 2% glucose]. Cultivation is generally carried out at a temperature of 15°–43° C. (optimally about 30° C.) for about 20–100 hours, if necessary with aeration and/or agitation. The technique of fed batch cultivation may also be used.

(ii) Step of Separating Coloring Contaminants from HSA

The step of separating coloring contaminants from HSA is incorporated into the cultivation step, purification step (after cultivation) or line step (in-line) and, in that step, an HSA-containing aqueous solution, such as the culture fluid, culture supernatant, crude fraction or purified fraction, is treated.

In accordance with the present invention, the coloration of human serum albumin is prevented by separating coloring contaminants from HSA before the both bind to each other. Therefore, in extracellular expression, in particular, the separation step desirably should be carried out during the cultivation step. In the case of intracellular expression, said separation step desirably should be performed during and/or immediately after the treatment of cells for obtaining HSA therefrom.

As the treatment for removing HSA from cells, there may be mentioned such conventional methods as the freeze-thaw method, glass bead method, high pressure method, sonication method and enzyme treatment method.

The means of separation may comprise, for example, removal of coloring contaminants by means of an adsorbent. An anion exchanger, hydrophobic carrier or activated charcoal is a desirable adsorbent. A cation exchanger or a clay mineral may further be used combinedly.

The anion exchanger includes, among others, DEAE-substituted matrices (e.g. DEAE-agarose, DEAE-substituted crosslinked dextran, DEAE-cellulose etc.) and QAE-substituted matrices (e.g. QAE-agarose, QAE-substituted crosslinked dextran etc.).

The "hydrophobic carrier" so called herein is a substance derived from an insoluble carrier by binding a hydrophobic ligand thereto. The hydrophobic ligand is, for example, an alkyl (e.g. in particular $C_{1-10}$ alkyl such as ethyl, butyl, octyl), phenyl or phenylalanyl. Specific examples thereof include alkyl agarose, alkyl crosslinked dextran, alkyl hydrophilic vinyl polymer, phenyl agarose, phenyl crosslinked dextran, phenyl hydrophilic vinyl polymer, phenylalanine agarose, phenylalanine crosslinked dextran, phenylalanine hydrophilic vinyl polymer. As the insoluble carrier, there may be mentioned, among others, agarose, crosslinked dextran and hydrophilic vinyl polymers.

Examples of clay minerals are activated clay, Japanese acid clay, bentonite, activated alumina and the like.

In the practice of the invention, it is desirable that the separation step be carried out in parallel with the cultivation step and human serum albumin be purified by a per se known method.

The treatment conditions of the separation step are preferably as follows:

pH; 4 to 8 (more preferably pH 5 to 6.5); and
Addition level: 0.01 to 10% (w/v; in the medium).

Further, addition of fatty acid, ethylenediamine, salicylic acid, aminoguanidine or the like to the culture medium before cultivation is also effective for preventing coloration of the recombinant HSA. Usable a fatty acid is a saturated or unsaturated one having from 14 to 20, preferably from 16 to 18 carbon atoms. Specific examples thereof are palmitic acid, stearic acid, oleic acid, linoleic acid, linolenic acid and the like. The amount of these additives is from 0.01 to 10 w/v%.

For the purification step, various fractionation methods, adsorption chromatography, affinity chromatography, gel filtration, density gradient centrifugation, dialysis and the like known methods may be employed. In the practice of the invention, the separation step may be combined with the purification step.

The method of this invention reduces the extent of coloration of genetically engineered HSA to about 1/70 to 1/10 as compared with the corresponding untreated HSA. The HSA recovery rate is satisfactory and the intrinsic properties of HSA do not undergo change.

In particular, the use of a pigment adsorbent for removal of coloring contaminants provides a simple and industrially efficient method.

The HSA product treated by the method of this invention can be used as a clinically useful medicine in quite the same manner as serum-derived HSA.

The following reference example, working examples, comparative example and test examples are further illustrative of the present invention but are by no means limitative of the scope thereof.

REFERENCE EXAMPLE

Preparation of *Saccharomyces cerevisiae* TMS33-1h4 for Secretory Expression of HSA

[i] Cloning of GAPDH promoter region, SUC2 signal region, LEU2 region, TRP1 region and PHO5 terminator region and preparation of HSA gene and G418 resistance gene The methods respectively described in the references cited below or modifications thereof were used or commercial products were purchased.

GAPDH promoter: Holland, H. J. and Holland, J. P., J. Biol. Chem., 254 (12), 5466 (1979); Holland, H. J. and Holland, J. P., J. Biol. Chem., 254 (19), 9839 (1979); JP-A-63-84498 corresponding to EP-A-248410.

SUC2 signal sequence: JP-A-60-41488 and 63-84498 corresponding to EP-A-127304 and EP-A-248410, respectively.

HSA gene: JP-A-62-29985 corresponding to EP-A-206733.

PHO5 terminator: JP-A-62-151183 corresponding to EP-A-216573.

G418 resistance gene: Oka, A., Sugisaki, H. and Takanami, M., J. Mol. Biol., 147, 217 (1981); Jimenez, A. and Davies, J Nature, 287, 869 (1980); JP-A-61-41793 or EP-A-163491;

TRP1: derived from the plasmid pBTI-10 (commercially available from Boehringer-Mannheim);

LEU2: derived from the plasmid pBTI-1 (commercially available from Boehringer-Mannheim);

*Escherichia coli* replication origin region and ampicillin resistance gene: derived from the plasmid pUC19 (commercially available from Takara Shuzo).

[ii] Construction of plasmids

Figure 1A:
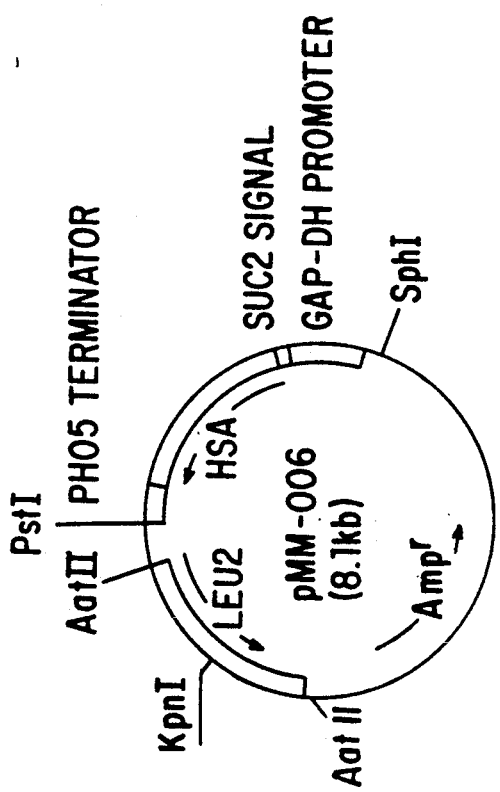

The construction of the plasmids pMM-006 and pHO-011 from pUC19 was carried out using the conventional methods described in "Molecular Cloning", Cold Spring Harbor Laboratory (1982) (see FIG. 1(a) and FIG. 1(b)).

The plasmid pMM-006 contains the leucine synthesis system gene LEU2 as a sequence homologous to a chromosomal sequence of the host yeast cell. In the plasmid the SUC2 signal sequence, structural gene for HSA and PHO5 terminator are joined together and placed under the control of the GAP-DH promoter.

The plasmid pHO-011 contains the tryptophan synthesis system gene TRP1 as a sequence homologous to a chromosomal sequence of the host yeast cell. In the plasmid, the SUC2 signal sequence, structural gene for HSA and PHO5 terminator are joined together and placed under the control of the GAP-DH promoter. The plasmid further contains the G418 resistance gene as a selective marker gene.

The plasmids pMM-006 and pHO-011 have been deposited with the Fermentation Research Institute, Agency of Industrial Science and Technology, Ministry of International Trade and Industry, Japan of 1-3, Higashi 1-chome, Tsukuba-shi, Ibaraki, Japan, since Apr. 28, 1989 under the Budapest Treaty as follows:

(1) Name of microorganism: pMM006/*E. coli* JM109
Deposit number: FERM BP-2404
(2) Name of microorganism: pHO011/*E. coli* HB101
Deposit number: FERM BP-2405

All restrictions on the availability of the above clones will be removed irrevocably upon allowance and issuance of the instant application into a United States patent. Access to the cultures will be available during the pendency of the patent application to those determined by the Commissionar of Patents and Trademarks to be entitled thereto. Should any culture become nonviable or be destroyed, it will be replaced.

[iii] Transformation of *S. cerevisiae* AH22 with plasmid pHO-011

The *S. cerevisiae* strain AH22 is a mating type and has mutations in the histidine synthesis system gene (his4) and leucine synthesis system gene (leu2). Therefore, it cannot grow unless histidine and leucine are added to the medium.

The plasmid pHO-011 for secretory expression of HSA was introduced into the chromosome of *Saccharomyces cerevisiae* AH22 by the following method which is the same as that described hereinlater in [v] except for the following:

Host: AH22.
Plasmid: pHO-011.
Plasmid introduction: The plasmid pHO-011 was linearized by digestion with EcoRV which cleaves the plasmid at the unique EcoRV site in the TRP1 gene thereof and then introduced into the host.

Transformation medium: Spheroplasts to be transformed were suspended in YPD liquid medium supplemented with 1.2 M sorbitol, 3% noble agar and 0.2% monopotassium phosphate. For plates, YPD liquid medium supplemented with 1.2 M sorbitol, 3% noble agar and 100 μg/ml G-418 was used.

Production of human serum albumin: 60 μg/ml.

One of the desired transformants thus obtained was named TMS-26-10.

[iv] Screening of transformant TMS-26-10.

(1) The site of introduction of the HSA gene was determinde by Southern blotting. The gene had been introduced into the TRP1region of the chromosome.

(2) The stability of the HSA gene was estimated with the HSA production and G418 resistance as indices. The HSA gene was retained 100% even after about 60 generations in a nonselective medium.

[v] Transformation of the transformant TMS-26-10 with the plasmid pMM-006

*Saccharomyces cerevisiae* AH22 transformant TMS-26-10 was cultured overnight with shaking at 37° C. in 50 ml of YPD liquid medium (YPD was prepared by dissolving 10 g of yeast extract and 20 g of Bacto-peptone in water to make 900 ml. The solution was autoclaved and when cooled mixed with 100 ml of separately autoclaved 20% glucose). The culture was centrifuged, cells thus obtained were suspended in 20 ml of water and the suspension was again centrifuged. The cells thus obtained were suspended in 10 ml of a solution containing 50 mM dithiothreitol, 1.2 M sorbitol and 25 mM EDTA, pH 8.5, and the suspension was shakened gently at 30° C. for 10 minutes. Cells were recovered by centrifugation and suspended in 10 ml of 1.2 M sorbitol. Again cells were collected by centrifugation and suspended in 10 ml of 1.2 M sorbitol.

The cells were collected by centrifugation and suspended in 10 ml of a solution containing 0.2 mg/ml Zymolyase 100T (Seikagaku Corporation), 1.2 M sorbitol, 10 mM EDTA and 0.1 M sodium citrate, pH 5.8. The suspension was shaken gently at 30° C. for 1 hour. Cells were recovered by centrifugation, washed with 10 ml of 1.2 M sorbitol and then with 10 ml of 10 mM calcium chloride plus 1.2 M sorbitol. Cells collected by centrifugation were suspended in 10 ml of 10 mM calcium chloride plus 1.2 M sorbitol.

A 100-μl portion of the suspension was placed into a sterilized test tube and mixed with 5 μl of a DNA solution (containing 5 μg of pMM-006 linearized by digestion with KpnI which cleaves at the unique KpnI site on the LEU2 gene) and the mixture was allowed to stand at room temperature for 15 minutes. To the mixture was added 1.2 ml of a solution of 20% polyethylene glycol 4000, 10 mM calcium chloride and 10 mM Tris-hydrochloride, pH 7.5. After gentle shaking, the resultant mixture was allowed to stand at room temperature for 20 minutes. Cells were collected by centrifugation and suspended in 0.1 ml of YPD liquid medium containing 1.2 M sorbitol and 10 mM calcium chloride and the suspension was shakened gently at 30° C. for 30 minutes.

Then 1.5, 10, 20 and 50 microliter portions of the suspension were mixed with an agar medium and the resultant suspension was spread on individual plates comprising 10 ml of a leucine-free medium maintained at 45° C. After solidification of the plates, the stationary cultures was maintained at 30° C. for 3 days. Each colony that formed was collected with a toothpick, suspended in 3 ml of 0.7% yeast nitrogen base plus 2% glucose, and shake-cultured at 30° C. for 2 days. A 1.5-ml portion of the culture was centrifuged and the cells collected were suspended in 3 ml of YPD liquid medium and shake-cultured at 30° C. The HSA concentration in the culture supernatant was measured by the RPHA method. On the third day, a maximum of 80 μg/ml of HSA was detected.

The thus-obtained transformant was named TMS-33-1.

[vi] Screening of transformant TMS-33-1 (stability of LEU2 gene and yield of HSA)

(1) The site of introduction of the HSA gene was determined by Southern blotting. It was found that the gene had been duly introduced into the LEU2 region of the chromosome.

(2) The stability of the HSA gene was estimated with yield of HSA and nonrequirement of leucine as indices. The HSA gene was retained 100% after about 60 generations in a nonselective medium.

Thus it could be confirmed that the strain TMS-33-1 contained the HSA gene introduced into the chromosome of the host yeast Saccharomyces cerevisiae AH22 at 2 sites thereof, namely in the LEU2 and TRP1 regions.

Furthermore, a revertant no longer requiring histidine, TMS-33-1h4, was obtained from the strain TMS-33-1 in the following manner. Strain TMS-33-1 was grown overnight in a nonselective medium and then cells were collected, washed thoroughly and spread on a selective plate (i.e. a plate comprising a histidine-free medium). The selective plate was incubated at 30° C. From among candidate revertants grown without requiring histidine, the strain TMS-33-1h4 was obtained.

In cultivating the strain TMS-33-1h4, various adsorbents for pigments were added to the culture fluid and their effects on the coloration of HSA were examined.

EXAMPLES 1 TO 4 AND COMPARATIVE EXAMPLES 1 TO 3

[i] Medium (1) YNB medium: Prepared by dissolving 6.7 g of Bacto-yeast nitrogen base (Difco) in 100 ml of distilled water, subjecting the solution to filter sterilization, mixing the same with a separately autoclaved solution (900 ml) containing 20 g of glucose (Nakalai-Tesque) in distilled water.

(2) Synthetic medium based on glucose-ammonium acetate having the composition shown below in Table 1:

TABLE 1

| Component | Concentration (mg/liter) |
|---|---|
| Glucose | 20,000 |
| $NH_4CH_2COO$ | 5,000 |
| $KH_2PO_4$ | 10,000 |
| $CaCl_2.2H_2O$ | 100 |
| KCl | 2,000 |
| NaCl | 100 |
| $MgSO_4.7H_2O$ | 2,000 |
| $ZnSO_4.7H_2O$ | 100 |
| $CuSO_4.5H_2O$ | 5 |
| $FeCl_3.6H_2O$ | 100 |
| Biotin | 0.1 |
| Vitamin $B_1$ | 10 |
| Vitamin $B_6$ | 1 |
| Sodium pantothenate | 10 |
| Inositol | 50 |

TABLE 1-continued

| Component | Concentration (mg/liter) |
|---|---|
| | pH 6.0 |

[ii] Cultivation

Preculture

An adequate amount of strain TMS-33-1h4 was inoculated into a baffled erlenmeyer flask containing YNB medium and shake-cultured at 30° C. for 24 hours.

Culture proper

Cells were collected by centrifuging the preculture fluid and suspended in 10 ml of sterile water. The glucose-ammonium acetate-based synthetic medium was inoculated with the cell suspension at an inoculum size of 1 ml per 100 ml of medium. The inoculated synthetic medium was distributed in 100-ml portions into 300-ml baffled erlenmeyer flasks and shake cultured at 30° C. and 125 rpm for 70 hours.

In that shake culture, the pigment-adsorbing adsorbents specified in Table 2 were added at an addition level of 1.0% (w/v). In a control run, the culture was performed without addition of any adsorbent.

TEST EXAMPLE 1

[i] Purification and Concentration of Culture Supernatant

After completion of the shake culture, each culture fluid was sampled, the sample was centrifuged at 15,000 rpm for 5 minutes and part of the supernatant obtained was subjected to HSA concentration determination.

Blue Cellulofine (Seikagaku Corporation; thoroughly washed with physiological saline; 1 g) was added, as a filter cake, to the remaining portions of the culture supernatant (about 100 ml) and albumin was allowed to be adsorbed on the cake at room temperature for 2 hours. The Blue Cellulofine with albumin adsorbed thereon was transferred to a minicolumn, washed with physiological saline and then eluted with 3 ml of 3 M sodium thiocyanate. The eluate was concentrated in a concentrator [Centricon 30 (30 K); Amicon] and the concentrate was used as a sample for assay.

[ii] Determination of HSA Concentration

The culture supernatant was assayed for HSA using the reversed passive hemagglutination test (RPHA test which utilizes hemagglutination between erythrocytes sensitized by an antibody and an antigen to the antibody). A standard HSA (Miles) was used for determining the HSA concentration in the culture supernatant by comparison therewith.

[iii] Comparison in Extent of Coloration

The purified and concentrated sample was subjected to absorbance measurements at the wavelengths of 280 nm, 350 nm and 405 nm, and the absorbance ratio between 350 nm and 280 nm and that between 405 nm and 280 nm were calculated. These values were used as indices of the degree of coloration.

The results obtained in the above manner are shown below in Table 2.

TABLE 2

| Example No. | Adsorbent | 350 nm/ 280 nm | 405 nm/ 280 nm | HSA concentration (μg/ml) |
|---|---|---|---|---|
| Control | None | 0.123 (100) | 0.112 (100) | 10 |
| Example 1 | Anion exchanger | 0.0073 (5.9) | 0.0036 (3.2) | 10 |
| Example 2 | Hydrophobic carrier | 0.0163 (13.3) | 0.0179 (16.0) | 10 |
| Example 3 | Mixture A | 0.012 (9.8) | 0.010 (8.9) | 10 |
| Comparative Example 1 | Cation exchanger | 0.128 (104) | 0.136 (121) | 7.5 |
| Comparative Example 2 | Mixture B | 0.085 (69.1) | 0.080 (71.4) | 7.5 |
| Comparative Example 3 | Mixture C | 0.083 (67.5) | 0.074 (66.1) | 7.5 |
| Example 4 | Mixture D | 0.0054 (4.4) | 0.0060 (5.4) | 7.5 |

Note: parenthetic value means percent coloration based on control

Anion exchanger: 1.0% Dowex 1X8.
Hydrophobic carrier: 1.0% XAD-2, Rohm and Haas.
Mixture A: The above anion exchanger/the above hydrophobic carrier (1/1).
Cation exchanger: 1.0% Dowex 50W-X8.
Mixture B: The above cation exchanger/the above anion exchanger (1/1).
Mixture C: The above cation exchanger/the above hydrophobic carrier (1/1).
Mixture D: The above cation exchanger/the above anion exchanger/the above hydrophobic carrier (1/1/1).

Each mixture was used at an addition level of 1.0% (w/v).

EXAMPLE 5

[i] Medium (1) Medium for batch culture: Having the composition shown in Table 3.
(2) Medium for feed culture: Having the composition shown in Table 4.

TABLE 3

| Component | Concentration (mg/liter) |
|---|---|
| Glucose | 1,000 |
| $(NH_4)_2SO_4$ | 2,000 |
| $KH_2PO_4$ | 20,000 |
| KCl | 4,000 |
| NaCl | 400 |
| $MgSO_4.7H_2O$ | 4,000 |
| $CaCl_2.2H_2O$ | 100 |
| $ZnSO_4.7H_2O$ | 100 |
| $CuSO_4.5H_2O$ | 10 |
| $FeCl_3.6H_2O$ | 100 |
| Biotin | 0.2 |
| Vitamin $B_1$ | 20 |
| Vitamin $B_6$ | 2 |
| Sodium pantothenate | 20 |
| Inositol | 100 |
| | pH 5.8 |

TABLE 4

| Component | Concentration (mg/liter) |
|---|---|
| Glucose | 500,000 |
| $MgSO_4.7H_2O$ | 20,000 |
| $ZnSO_4.7H_2O$ | 1,000 |
| $CaCl_2.2H_2O$ | 300 |
| $CuSO_4.5H_2O$ | 50 |
| Biotin | 1 |
| Vitamin $B_1$ | 100 |

TABLE 4-continued

| Component | Concentration (mg/liter) |
|---|---|
| Vitamin $B_6$ | 10 |
| Sodium pantothenate | 100 |
| Inositol | 500 |

[ii] Cultivation

Preculture

A baffled erlenmeyer flask containing YNB medium was inoculated with 1 ml of the glycerol-frozen stock strain ($OD_{540} = 10$) and shake cultured at 30° C. for 24 hours. Cells were collected by centrifugation and suspended in sterile water, and the suspension was inoculated into 4 liters of batch culture medium.

Culture proper

The cultivation was performed with aeration and agitation using a 10-liter mini-jar fermentor. The aeration was conducted at 1 vvm and the rate of agitation was controlled such that the dissolved oxygen concentration remained at a level not less than 10 ppm. The pH was maintained at a constant level of 5.8 by addition of 28% aqueous ammonia. For defoaming, an antifoam (Adekanol; Asahi Denka Kogyo) was added in small quantities as necessary.

A control program was used in adding 4 liters of the feed medium so that the specific growth rate could be maintained at 0.12 $hr^{-1}$.

Culture-controlling program

The program was used to control the rate of feeding of the feed medium during cultivation. This program was designed such that, normally, the rate of addition of the feed medium could be determined to give a specific growth rate of 0.12 $hr^{-1}$ and that when the dissolved oxygen concentration decreased to 2 ppm or below during cultivation control, constant rate fed culture should proceed with the specific rate of growth being set at 0.

Pigment-adsorbing adsorbent

Eight grams (8 g) of powdered activated charcoal (Wako Pure Chemical Industries) was added to the batch culture medium to give a final concentration of 0.1% (w/v; 8 g/8 liters).

In a control run, the cultivation was performed without adding the activated charcoal.

TEST EXAMPLE 2

[i] Measurement of Cell Concentration

The culture fluid was sampled at an optionally selected time point during cultivation. The sample was diluted adequately with distilled water and subjected to absorbance measurement at 540 nm using a spectrophotometer (Shimadzu model UV240). Dry cell weight (DCW) was estimated using a working curve prepared in advance.

HSA concentration determination and comparison in degree of coloration were carried out as mentioned hereinabove. The HSA concentration in each sample was expressed in mg/liter.

The results thus obtained are shown in Table 5.

TABLE 5

| | Control | Example 5 |
|---|---|---|
| Cultivation period (hr) | 71 | 69.5 |
| $OD_{540}$ | 956.0 | 976.0 |
| Cell concen- | 119.5 | 122.0 |

TABLE 5-continued

|  |  | Control | Example 5 |
|---|---|---|---|
| tration (g/DCW/liter | | | |
| HSA concentration (mg/ml) | | 800 | 800 |
| Degree of coloration | 350 nm/ 280 nm | 0.158 (100) | 0.0035 (2.2) |
| | 405 nm/ 280 nm | 0.125 (100) | 0.0018 (1.4) |

Note: parenthetic value means percent coloration based on control.

The course of cultivation was smooth even in the presence of 0.1% (w/v) of activated charcoal and, after 70 hours of cultivation, the cell weight amounted to 120 g-DCW/liter and the production of HSA to 800 mg/liter.

Thus, even in the presence of 0.1% (w/v; 1 g/liter) of activated charcoal, it was possible to carry out cultivation in the same manner as ordinary cultivation. Furthermore, the degree of coloration of the product HSA was as small as 1 to 2% as compared with the control.

While the invention has been described in detail and with reference to specific examples thereof, it will be apparent to one skilled in the art that various changes and modifications can be made therein without departing from the spirit and scope thereof.

What is claimed is:

1. A process of inhibiting the coloration of recombinant human serum albumin produced by tranformed cells propagated in a liquid culture medium, comprising culturing said cells in said medium in the presence of an absorbent which binds coloring contaminants so as to separate said coloring contaminants from said albumin.

2. The process of claim 1, wherein said absorbent is an anion exchanger selected from the group consisting of diethylaminoethyl (DEAE)-substituted matrices, quaternary aminoethyl (QAE)-substituted matrices and $CH_2N(CH_3)_3$ substituted matrices, a hydrophobic carrier having a phenyl group as a ligand, activated charcoal or combination thereof.

3. The process of claim 2, wherein the transformed cells secrete human serum albumin.

4. The process of claim 2, wherein the transformed cells do not secrete human serum albumin.

5. The process of claim 3, wherein an anion exchanger is employed in the culturing step.

6. The process of claim 3, wherein a hydrophobic carrier is employed in the culturing step.

7. The process of claim 3, wherein active carbon is employed in the culturing step.

8. The process of claim 4, wherein an anion exchanger is employed in the culturing exposing step.

9. The process of claim 4, wherein a hydrophobic carrier is employed in the culturing step.

10. The process of claim 4, wherein active carbon is employed in the culturing step.

* * * * *